| United States Patent [19] | [11] | Patent Number: | 4,748,144 |
|---|---|---|---|
| Monnier et al. | [45] | Date of Patent: | May 31, 1988 |

[54] DELAFOSSITE MIXED METAL OXIDE CATALYSTS AND METHOD FOR THEIR PREPARATION

[75] Inventors: John R. Monnier, Fairport; Gustav R. Apai, II; Michael J. Hanrahan, both of Rochester, all of N.Y.

[73] Assignee: Eastman Kodak Company, Rochester, N.Y.

[21] Appl. No.: 896,044

[22] Filed: Aug. 13, 1986

[51] Int. Cl.$^4$ .................. B01J 21/04; B01J 23/72; B01J 23/86
[52] U.S. Cl. ........................... 502/316; 502/331
[58] Field of Search ................. 502/316, 331

[56] References Cited

U.S. PATENT DOCUMENTS

| 2,544,756 | 3/1951 | Guest et al. | 502/316 |
| 2,767,202 | 10/1956 | Rottig et al. | 502/331 X |
| 4,144,198 | 3/1979 | Miya et al. | 502/331 |

*Primary Examiner*—W. J. Shine
*Attorney, Agent, or Firm*—Stephen E. Reiter; J. Jeffrey Hawley; Joshua G. Levitt

[57] ABSTRACT

Catalysts for the conversion of synthesis gas to linear alcohols and aldehydes are disclosed. The catalysts are mixed oxides of copper, iron and either chromium or aluminum and wherein said mixed oxide has a delafossite type of crystal lattice structure.

4 Claims, 1 Drawing Sheet

DELAFOSSITE MIXED METAL OXIDE CATALYSTS AND METHOD FOR THEIR PREPARATION

FIELD OF THE INVENTION

The present invention relates to catalyst compositions. The compositions of the invention are useful in the conversion of synthesis gas to linear alcohols and aldehydes in high proportion relative to linear hydrocarbons.

BACKGROUND OF THE INVENTION

The production of chemicals by the gasification of coal has been a goal of research for many years. In particular, it has been desired to produce linear oxygenates (e.g. alcohols and aldehydes) from carbon monoxide and hydrogen. Usually, the production of these desirable compounds is accompanied by the production of linear hydrocarbons, usually n-paraffins.

Many catalysts have been suggested to perform this conversion. In U.S. Pat. Nos. 4,122,110 and 4,291,126 there are disclosed catalysts which are said to be capable of converting synthesis gas to oxygenates in yields over 90%. These catalysts are four component mixtures which include copper, cobalt, a third metal selected from chromium, iron, vanadium and manganese, and at least one alkali metal. Coprecipitation techniques are used and the resultant catalyst is dried at 200°–600° C. Attempts to repeat these results by others have not been successful. References are made to Courty et al, "$C_1$–$C_6$ Alcohols Production from Syngas", Symposium on Chemicals from Syngas and Methanol, 191$^{st}$ ACS National Meeting, Apr. 13–18, 1986 and Courty et al, J. Molec. Catal. 17, 241 (1982).

Other catalysts have also been suggested. In U.S. Pat. No. 4,440,668, there is disclosed a catalyst which contains copper, cobalt, an alkali metal and zirconium.

In U.S. Pat. No. 4,119,656, there is disclosed a catalyst that includes palladium.

In French Pat. No. 1,074,045 there is disclosed the use of precipitated catalysts which include a major portion of copper and a minor portion of a metal of the iron group with the possible addition of activators such as alkali metals, zinc or chromium. A mixture of the oxides of copper, iron and potassium is disclosed. However, there is no disclosure of the crystal structure of these catalysts.

The present invention provides an alternative catalyst of unique crystal structure. The catalysts of the present invention display excellent selectivity to the production of higher oxygenates.

SUMMARY OF THE INVENTION

In accordance with the present invention, there is provided a mixed oxide of copper, iron and either chromium or aluminum and wherein said mixed oxide has a delafossite type of crystal lattice structure said mixed oxide having an onset of reduction at a temperature less than 350° C. and a maximum rate of reduction at a temperature greater than 350° C. when heated at 5° C. per minute in the presence of hydrogen at atmospheric pressure.

In preferred embodiments, the mixed oxide is promoted with an alkali metal such as potassium.

BRIEF DESCRIPTION OF THE DRAWING

The FIGURE is a graph showing the temperature programmed reduction of three catalysts within the scope of the invention and two controls.

DETAILED DESCRIPTION OF THE INVENTION

Figure 1:
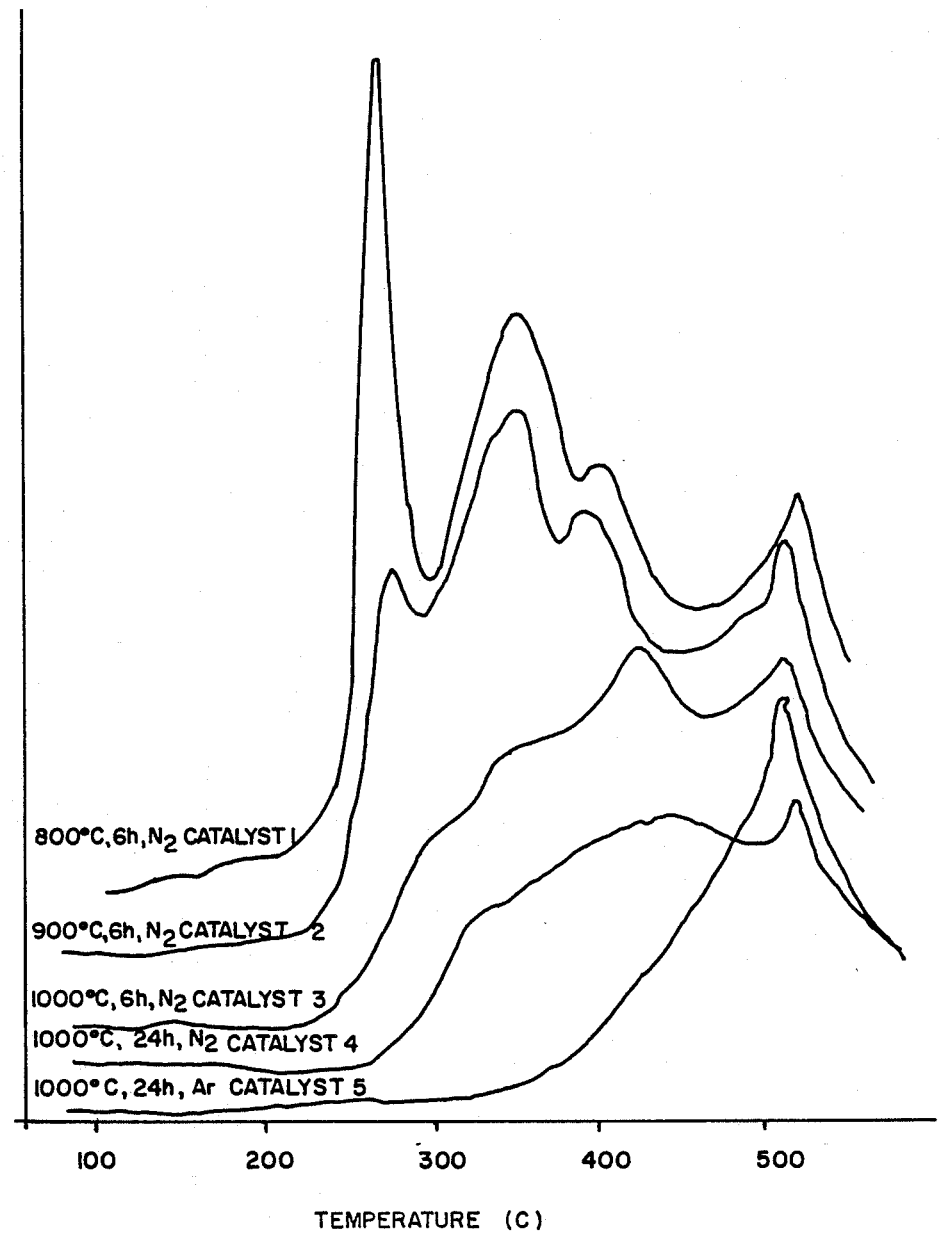

The mixed oxides of the present invention should be distinguished from simple mixtures of the oxides, which mixtures are known in the art. The mixed oxides used herein have a delafossite type of crystal structure. In a simple mixture of the oxides, no homogeneous crystal lattice is formed. In the mixed oxides of the present invention, a true crystal is formed having specific components repeatably occurring in a regular lattice structure.

A delafossite type structure is known in the art for other components. Reference is made to Garcia et al, J. Electrochem Soc. 127, 1974 (1980) and Shannon et al, Inorg. Chem. 10 713 (1971) for a description of this type of lattice structure.

For the present copper-iron mixed oxides, the presence of the desired delafossite type of crystal structure can be confirmed by x-ray diffraction analysis. Powder x-ray diffraction patterns can be obtained over a $2\theta$ range of 4°–70° using a Siemen's D500 diffractometer, with $CuK\alpha$ radiation, diffracted beam graphite monochromator and scintillation detector. Data can be analyzed using Siemen's Diffrac XI software.

The delafossite phase is characterized by a diffraction pattern which has peaks at $2\theta$ values of about 16, 31, 36, 56, 62 and 65. When higher temperatures are used in making the catalyst, as will be discussed more fully below, the peaks for the delafossite phases of the Cu-$FeO_2$ and the $CuMO_2$ tend to merge forming what will be referred to as a "perfect" delafossite.

The mixed oxide can be represented by the formula:

$$Cu_xM_aFe_bO_{2x}$$

wherein M is selected from the group consisting of Cr and Al and a+b is equal to or almost equal to x.

As noted in the formula above, the value for a+b is equal to or almost equal to x. If this value is exactly equal to x, then we have found that a "perfect" crystal structure might result and the catalyst could be inactive under certain preparation conditions mentioned below. The exact value for a+b as well as process parameters for making the catalyst are determined by a simple experiment such that onset of reduction and maximum rate of reduction fall within the described limits.

The catalysts are useful according to the invention if, in a simple temperature programmed reduction experiment, the onset of reduction occurs at a temperature of less than 350° C. If the onset of reduction is at a temperature greater than 350° C., this means that there are too few crystal imperfections for the catalyst to be active under reaction conditions. Also, the maximum rate of reduction must be at a temperature greater than 350° C. If the maximum rate is at a temperature less than 350° C., then there is too much Fe° formed (reduces at less than 300° C.) and the catalyst performs like a conventional copper-iron catalyst.

The temperature programmed reduction is carried out using conventional techniques. The sample is heated at a controlled rate in hydrogen and the amount of evolved water is monitored. The water can be measured by any convenient method, for example, mass spectroscopy, gas chromatography or infrared analysis.

In a typical analysis, a 0.5 g sample of the catalyst to be analyzed is pretreated by heating at 300° C. in one atmosphere of flowing helium for one hour. This treatment removes any water that might be in the sample. Then, the sample is allowed to cool to room temperature and the helium replaced by hydrogen. The sample is then heated at 5° C./min up to about 500° C. During this process, the amount of water in the flowing gas is monitored. The amount of water can be plotted against the temperature of the sample to obtain a plot like FIG. 1.

The mixed oxide delafossite crystals of the present invention are made by heating a stoichiometric mixture of the oxides at elevated temperature in an inert atmosphere. Useful temperatures are from about 800° C. to about 1100° C. A preferred range of temperature is from 900° to 1000° C. The atmosphere can be any inert gas such as helium, argon or nitrogen. The gas should be substantially free from oxygen since oxygen appears to inhibit the formation of the desired delafossite phase. However, a small amount of oxygen, e.g. 2000 ppm, is desirable in order to prevent the formation of a perfect delafossite phase. The heating time for formation of the desired crystals is from about 4 hours to 24 hours.

After cooling, the resulting powder can be used directly as a synthesis gas catalyst. In preferred embodiments, a minor amount of alkali metal can be added to the powder as a promoter. The alkali metal can be used in the form of the hydroxide or other common salt. Incorporation of the alkali metal is conveniently done by the impregnation of the catalyst with a solution of the alkali metal.

One particularly convenient method of adding the alkali metal promoter is to form a solution of the desired amount of the metal ethoxide in ethanol. Then, this solution is mixed with the catalyst and the ethanol is removed, for example, by rotary evaporation. The resulting powder is then dried, for example, in nitrogen at 120° C.

The amount of alkali metal promoter is typically between $4.0 \times 10^{-5}$ moles of alkali per gram of catalyst to about $1.0 \times 10^{-3}$ moles.

It is preferred to subject the catalyst before use to a preliminary reduction treatment as is common in this art. The reduction treatment can be in hydrogen or a combination of hydrogen and synthesis gas or hydrogen and an inert gas such as nitrogen, helium or argon. Suitable temperatures for this treatment are from 225° to 300° C. Normally, the temperature will be raised progressively over the period of pretreatment, which period is usually from about 2 hours to 4 hours.

The mixed oxides of the present invention can be used in the conventional synthesis gas process for the production of alcohols. The reaction temperatures will normally be in the range of 225° to 300° C. and preferably between 250° and 270° C. The pressures will normally be in the range of 0.1 to 10 MPa. High exit space velocities are normally used, for example, from between 8000 and 40000 hr$-1$. In general, the exit space velocities are high enough to maintain the CO conversion levels to less than 2%.

The following examples are presented for a further understanding of the invention.

EXAMPLE 1

Preparation and Catalytic Activity of $Cu_2FeCrO_4$

To a quartz ampoule, $Cu_2O$ (1.431 g, 0.01 moles), $Fe_2O_3$ (0.799 g, 0.005 moles), and $Cr_2O_3$ (0.760 g, 0.005 moles) were added and thoroughly mixed. The sample was evacuated to $5 \times 10^{-2}$ torr at 150° C., cooled in vacuo to 25° C., and sealed in vacuo. The evacuated mixture was heated to 600° C. for 4 hours and then to 900°-1000° C. for 15 hours. The sample was removed from the furnace and allowed to cool before being opened. X-ray diffraction analysis indicated the material exhibited a mixed delafossite lattice structure and x-ray photoelectron spectroscopy (XPS) revealed that the Cu present in the catalyst was essentially 100% $Cu^+$, while the Fe was present as $Fe^{3+}$. Following reduction in flowing $H_2$ at 1 atmosphere pressure and 285° C. for 2 hours, XPS revealed that approximately 50% of the Cu was present as $Cu^\circ$ and 50% as $Cu^+$, while the Fe remained in a high oxidation state as $Fe^{2+}$ and/or $Fe^{3+}$, most probably as $Fe^{3+}$. The catalytic activity of the $H_2$-reduced catalyst (0.300 g) was determined at 250° C., 800 psig overall pressure, and $H_2/CO = 1/1$. Space velocities were kept high enough to maintain CO conversion levels $\leq 2\%$. The molar selectivity of oxygenates produced (moles of oxygenates formed divided by total moles of product formed) was 32%.

EXAMPLE 2

Preparation and Catalytic Activity of K-Promoted $Cu_2FeCrO_4$

A round-bottom, single-neck flask was charged with 1.0 g of $Cu_2FeCrO_4$ (prepared as in Example (1) and 25 ml of absolute ethyl alcohol. While swirling the contents of the flask, a predetermined number of moles of $K^+OEt^-$ in ethanol was added to the flask. After stirring for 15 minutes, the excess $C_2H_5OH$ solvent was removed by rotary evaporation at 60° C. The catalyst was then dried in flowing $N_2$ at 100° C. before being loaded into the reactor.

The following loadings of KOEt per gram of $Cu_2FeCrO_4$ were prepared and evaluated for catalytic activity: $4.1 \times 10^{-5}$ moles, $2.05 \times 10^{-4}$ moles, $4.1 \times 10^{-4}$ moles, and $8.2 \times 10^{-4}$ moles.

All catalytic evaluations were carried out using the reaction conditions detailed in Example 1.

The product distributions can be represented in terms of weight percentage, in which the weight of a particular product formed during reaction is expressed as a percentage of the total weight of products formed during reaction. Table I shows the weight percentages of products formed using $Cu_2FeCrO_4$ promoted with $4.1 \times 10^{-4}$ moles KOEt/g catalyst.

TABLE I

| Weight Percentages of Products Formed During Synthesis Gas Conversion Over K-Promoted $Cu_2FeCrO_4$. Level of KOEt Promotion = $4.1 \times 10^{-4}$ moles/g Catalyst | |
|---|---|
| Oxygenates | wt % |
| $CH_3OH$ | 2 |
| $CH_3CHO$ | 12 |
| $C_2H_5CHO$ | 13 |
| $n-C_3H_7CHO$ | 12 |
| $n-C_4H_9CHO$ | 9 |
| TOTAL | 48% |
| Hydrocarbons | |
| Olefins | Paraffins |

TABLE I-continued

Weight Percentages of Products Formed During Synthesis Gas Conversion Over K-Promoted $Cu_2FeCrO_4$. Level of KOEt Promotion = $4.1 \times 10^{-4}$ moles/g Catalyst

| | wt % | | wt % |
|---|---|---|---|
| | | $CH_4$ | 6 |
| $C_2H_4$ | 5 | $C_2H_6$ | 3 |
| $C_3H_6$ | 7 | $C_3H_8$ | 4 |
| $1\text{-}C_4H_8$ | 7 | $n\text{-}C_4H_{10}$ | 4 |
| $1\text{-}C_5H_{10}$ | 5 | $n\text{-}C_5H_{12}$ | 3 |
| $1\text{-}C_6H_{12}$ | 4 | $n\text{-}C_6H_{14}$ | 2 |
| TOTAL | 28% | TOTAL | 22% |

In comparison to the results from Example 1, the alkali promotion decreased the percentage of methanol produced and correspondingly increased the percentages of other oxygenates.

EXAMPLE 3

Preparation and Catalytic Activity of Li-Promoted $Cu_2FeCrO_4$ and Cs-Promoted $Cu_2FeCrO_4$ The same experimental procedure was followed as for Example 2, except LiOEt and CsOEt were used in place of KOEt. For both LiOEt and CsOEt, the level of promotion was $4.1 \times 10^{-4}$ moles/g catalyst. These results were similar to Example 2.

EXAMPLE 4

Preparation and Catalytic Activity of Various K Salts as Promoters for $CU_2FeCrO_4$ The same experimental procedure was followed as for Example 2, except that, in addition to KOEt dissolved in ethanol, the promoters were KOH dissolved in $H_2O$ and $K[B(C_2H_5)_3H]$ dissolved in tetrahydrofuran. All promoters were added at the level of $4.1 \times 10^{-4}$ moles/g of catalyst. These results were also similar to Example 2.

EXAMPLE 5

Preparation and Catalytic Activity of $Cu_2FeAlO_4$

The same experimental procedure was followed as in Examples 1 and 2 except that $Al_2O_3$ (0.510 g, 0.005 moles) was used in place of $Cr_2O_3$. The catalytic activities were similar to Examples 1 and 2.

EXAMPLE 6

Preparation of $Cu_2FeCrO_4$ at High Temperatures in Flowing Helium

The same quantities of starting materials were used as in Example 1. Instead of synthesis in vacuo, the three metal oxides were thoroughly mixed and placed in a quartz U-tube through which a flow of 40 ml (STP) of He/min was passed as the catalyst was heated to 1000° C. and held at that temperature for 18 hours. At the end of this time, the sample was cooled in the flowing He to 25° C. and evaluated for catalytic activity. The catalytic activity for this catalyst and its potassium promoted counterpart were similar to previous results.

EXAMPLE 7

Effect of Temperature on $Cu_2FeCrO_4$ Preparation

A stoichiometrically correct mixture of the simple metal oxides was made according to the following procedure. Cuprous (I) oxide (99%), ferric (III) oxide (99.9%) and chromium (III) oxide (99%) were separately ground and sieved to give <75 μm diameter particles. The powders were combined at a weight ratio of 1.88 to 1.05 to 1 for $Cu_2O$, $Fe_2O_3$ and $Cr_2O_3$, respectively. The resulting powder was mixed by mechanical agitation until a visibly homogeneous powder resulted.

A series of mixed-delafossite catalysts was made under varying reaction conditions as detailed in Table II below. Generally, an aliquot of the above powder was placed in a u-shaped quartz reactor tube. The sweep gas (i.e., $N_2$ or Ar) was passed through the reactor tube at 40–60 standard cubic centimeters per minute (sccm) for at least 6 hours prior to heating. The reactor assembly was placed in a Fischer Model 497 Ashing Furnace. While maintaining the sweep gas, the oxide mixture was heated at 10° C. per minute from ambient to reaction temperature where the temperature was held for the specified time. The reactin was quenched by turning off the furnace and opening the furnace door. The temperature was found to decrease by $\simeq 400°$ C. within two minutes. When the resulting solid had cooled to room temperature, it was removed from the reactor tube.

Samples of the above catalysts were promoted with potassium at loadings of $8.7 \times 10^{-4}$ moles of potassium per gram of catalyst. Details of the procedure used to impregnate the catalysts with potassium may be found in Example 2.

Discussion of Results

The x-ray diffraction (XRD) pattern of the catalyst synthesized at 800° C. for six hours in $N_2$ prior to reduction shows the presence of two distinct delafossite phases and a minor metallic copper component. The delafossites were identified as $CuFeO_2$ and $CuCrO_2$. The separation of these phases is most obvious in areas of the pattern in the regions of $2\theta = 36°$, 40° and 61°. The peak at 31.3° is a nearly identical match for both phases (i.e., $2\theta$ for $CuCrO_2$ and $CuFeO_2$ and 31.39° and 31.27°, respectively) so that peak separation is not observed. The metallic copper assignment is confirmed by the presence of two peaks (at $2\theta = 43.5°$ and 51°).

The catalyst which was synthesized at 900° C. for six hours in $N_2$ gave essentially the same XRD pattern as the previous catalyst. The pattern obtained shows that the delafossite patterns were beginning to merge.

When the preparation temperature was increased to 1000° C. for six hours in $N_2$, some dramatic changes occurred in the XRD patterns of the resulting catalyst. The pattern obtained shows the presence of one delafossite phase. Two different peak shapes associated with the delafossite can be seen (cf. 15.6° and 31.4° with 36.4°, 55.9°, 62.4° and 65.5°). This phenomena was not as apparent in the previous two samples due to peak multiplicity. The delafossite crystals were found to be platelets when examined by transmission electron microscopy. The differences in peak shape were apparently the result of the directional crystallite size differences within the platelets. Reduction in hydrogen at 500° C. results in the formation of some Fe° and Cu° as well as small levels of $CuFe_2O_4$ as previously seen for samples prepared at lower temperature. The novel aspect of this catalyst is the retention of a crystalline delafossite phase matching $CuCrO_2$. It appears that the crystallinity of the delafossite phase benefits from enhanced stability when prepared at 1000° C. The signal intensity of Fe° is also substantially lower relative to the Cu° signal, indicating reduced formation of crystalline Fe°.

The XRD pattern of the catalyst prepared at 1000° C. in N₂ for 24 hours was also studied. Other than minor variations in relative peak intensities, these results are the same as those found in the previous sample which was prepared at 1000° C. for six hours in N₂. Indeed, as later discussions will show, both catalytic materials are strikingly similar. It was anticipated that the extended reaction time would result in a more uniform mixed delafossite.

In fact, when argon was substituted for nitrogen, a more "perfect" mixed delafossite was obtained under similar reaction conditions. The formation of the "perfect" mixed delafossite appears to prevent the formation of crystalline Fe° under reducing reaction conditions. This catalyst is not very active in comparison to the "imperfect" crystal structure materials previously described and is not within the scope of the invention. The temperature programmed reduction of this catalyst shows an onset of reduction at a temperature higher than 350° C. as shown in FIG. 1 as described in Example 8. Analysis for the presence of oxygen in the nitrogen used revealed oxygen levels of 2000 ppm. The manufacturers specifications for residual oxygen in bottled argon are less than 200 ppm. The presence of oxygen at the 2000 ppm level therefore prevents the formation of a "perfect" mixed delafossite.

The catalytic activities of these catalysts were determined before and after potassium promotion. Molar selectivities for these catalysts are tabulated in Table II.

The catalysts in FIG. 1 are those identified in Table II. Note the control catalyst 1 has a maximum rate of reduction at temperatures less than 350° C. and control catalyst 5 has an onset of reduction at a temperature greater than 350° C.

The invention has been described in detail with particular reference to preferred embodiments thereof, but it will be understood that variations and modifications can be effected within the spirit and scope of the invention.

What is claimed is:

1. A mixed oxide of the formula:

$$Cu_xM_aFe_bO_{2x}$$

wherein M is either chromium or aluminum and a+b is equal to or almost equal to x; wherein said mixed oxide has a delafossite type of crystal lattice structure; and wherein said mixed oxide has an onset of reduction at a temperature less than 350° C. and a maximum rate of reduction at a temperature greater than 350° C. when heated at 5° C. per minute in the presence of hydrogen at atmospheric pressure.

2. A mixed oxide according to claim 1 wherein said mixed oxide is promoted with an alkali metal.

3. A mixed oxide according to claim 2 wherein said alkali metal is potassium.

4. A method for the preparation of a mixed oxide of the formula:

TABLE II

| | Molar Selectivities for Cu₂FeCrO₄ at Steady State[1] | | | | | |
|---|---|---|---|---|---|---|
| | Mole % Selectivity[2] | | | | | |
| | Unpromoted | | | Promoted | | |
| Catalyst | CH₃OH | P + O[3] | A + A[4] | CH₃OH | P + O | A + A |
| 1 Control 800° C./6 hr/N₂ | 29.6 | 54.5 | 15.9 | 4.8 | 68.2 | 27.0 |
| 2 Invention 900° C./6 hr/N₂ | 28.9 | 57.3 | 13.8 | 4.3 | 66.6 | 29.1 |
| 3 Invention 1000° C./6 hr/N₂ | 34.5 | 51.7 | 19.7 | 2.8 | 57.6 | 39.7 |
| 4 Invention 1000° C./24 hr/N₂ | 34.9 | 52.2 | 13.1 | — | — | — |
| 5 Control 1000° C./24 hr/Ar. | 61.1 | 31.6 | 7.2 | — | — | — |

[1]Determined at 800 psig, 1/1 H₂/CO, 250° C.
[2](Particular product/total product) × 100 in terms of moles.
[3]P + O refers to the parafins and olefins produced.
[4]A + A refers to the higher oxygenates (alcohols and aldehydes) produced.

EXAMPLE 8

Catalyst preparations previously described in Example 7 were subjected to temperature programmed reduction. Heating was at 5° C./minute and water evolution was measured using mass spectroscopy. The results are plotted in FIG. 1. (Since the absolute amount of water evolution is not important, no scale is placed on the y axis and curves have been vertically separated for greater clarity.)

$$Cu_xM_aFe_bO_{2x}$$

wherein M is either chromium or aluminum and a+b is equal to or almost equal to x; wherein said mixed oxide has a delafossite type of crystal lattice structure, said method comprising the steps of:

(a) mixing oxides of Cu, Fe and M, and thereafter (b) heating said mixture at a temperature in the range of 900° to 1000° C. for a time sufficient to produce said delafossite type of crystal lattice structure.

* * * * *